US011078515B2

(12) United States Patent
Harer et al.

(10) Patent No.: US 11,078,515 B2
(45) Date of Patent: Aug. 3, 2021

(54) METHODS FOR IDENTIFYING TARGETS FOR ANTIMICROBIAL AND ANTIPROLIFERATIVE COMPOUNDS AND COMPOSITIONS THEREFROM

(71) Applicant: MIMETICS, LLC, Durham, NC (US)

(72) Inventors: John Harer, Chapel Hill, NC (US); Steven B. Haase, Pittsboro, NC (US)

(73) Assignee: MIMETICS, LLC, Durham, NC (US)

( * ) Notice: Subject to any disclaimer, the term of this patent is extended or adjusted under 35 U.S.C. 154(b) by 0 days.

(21) Appl. No.: 15/572,899

(22) PCT Filed: May 11, 2016

(86) PCT No.: PCT/US2016/031712
§ 371 (c)(1),
(2) Date: Nov. 9, 2017

(87) PCT Pub. No.: WO2016/183119
PCT Pub. Date: Nov. 17, 2016

(65) Prior Publication Data
US 2018/0119136 A1    May 3, 2018

Related U.S. Application Data

(60) Provisional application No. 62/179,545, filed on May 11, 2015.

(51) Int. Cl.
*C12Q 1/18* (2006.01)

(52) U.S. Cl.
CPC ........... *C12Q 1/18* (2013.01); *G01N 2333/38* (2013.01); *G01N 2333/39* (2013.01); *G01N 2333/40* (2013.01)

(58) Field of Classification Search
CPC .. A01H 1/04; C12N 15/1034; C12N 15/8241; C12N 15/8265; C12N 15/8287; C12Q 1/6883; C12Q 2600/158; G01N 21/6486; Y02A 90/22; Y02A 90/24; Y02A 90/26
See application file for complete search history.

(56) References Cited

FOREIGN PATENT DOCUMENTS

| WO | WO 98/42875 | 10/1998 |
|----|-------------|---------|
| WO | WO 02/016940 | 2/2002 |
| WO | WO 02/46465 | 6/2002 |
| WO | 02/081734 | 10/2002 |
| WO | WO 05/077181 | 8/2005 |

OTHER PUBLICATIONS

Agarwal et al. J. Biol. Chem. 278: 34998-35015, 2003.*
Chen et al. mBio 5: e01087-13, pp. 1-10, Feb. 4, 2014.*
Frazzitta A.E. et al., "Nitrogen source-dependent capsule induction in human-pathogenic *Cryptococcus* species", *Eukaryotic Cell*, vol. 12, No. 11, pp. 1439-1450 (2013).
Griffiths E.J. et al., "A defect in ATP-citrate lyase links acetyl-CoA production, virulence factor elaboration and virulence in *Cryptococcus neoformans*", *Molecular Microbiology*, vol. 86, No. 6, pp. 1404-1423 (2012).
Heiser L.M. et al., "Subtype and pathway specific responces to anticancer compounds in breast cancer", *PNAS*, vol. 109, No. 8, pp. 2724-2729 (2012).
Hu G. et al., "Metabolic adaptation in Cryptococcus neoformans during early murine pulmonary infection.", *Mol. Microbiol.*, vol. 69, No. 6, pp. 1456-1475 (2008).
Malouin F. et al., "Identification of antimicrobial compounds active against intracellular *Staphylococcus aureus*", *FEMS Immunology and Medical Microbiology*, vol. 45, No. 2, pp. 245-252 (2005).
Pellegrini P. et al., "A drug-screening model to identify compounds active in cells under metabolic stress", *Front. Pharmacol. Conference Abstract: 4th Annual Meeting of the International Society of Proton Dynamics in Cancer*, (2013), Abstract only.
Notification Concerning Transmittal of International Preliminary Report on Patentability and Written Opinion corresponding to International Patent Application No. PCT/US2016/031712, dated Nov. 14, 2017, 11 pages.
Williams, V. et al. "Role of Glucose in the Expression of *Cryptococcus neoformans* Antiphagocytic Protein 1, App1", *Eukaryotic Cell*, p. 293-301 (Mar. 2011).
Boiteux "Metabolic Studies on Synchronized Yeast Cells in Continuous Culture" Folia Microbiol., 39(6):509-511 (1994).
Walker "Synchronization of yeast cell populations" Methods in Cell Sci., 21:87-93 (1999).
Adams et al. "Asexual Sporulation in Aspergillus nidulans" Microbiol Mol. Biol Rev., 62:35-54 1998.
Cano and Ruiz-Herrera "Developmental Stages during the Germination of Mucor Sporangiospores" Exp Mycol., 12:47-59 1988.
Corbacho et al. "Standard YPD, even supplemented with extra nutrients, does not always compensate growth defects of *Saccharomyces cerevisiae* auxotrophic strains" Antonie van Leeuwenhoek, 99:591-600 2011.
Duina et al. "Budding Yeast for Budding Geneticists: A Primer on the *Saccharomyces cerevisiae* Model System" Genetics, 197:33-48 2014.
Garay-Arroyo et al. "Response to different environmental stress conditions of industrial and laboratory *Saccharomyces cerevisiae* strains" Appl. Microbiol, Biotechnol., 63:734-741 2004.
Hahn-Hägerdahl et al. "Role of cultivation media in the development of yeast strains for large scale industrial use" Microbial Cell Factories, 4(31):1-16 2005.
Herskowitz, I. "Life Cycle of the Budding Yeast *Saccharomyces cerevisiae*" Microbiological Rev., 52(4):536-553 1988.
Kim and Rose "Stable Pseudohyphal Growth in Budding Yeast Induced by Synergism between Septin Defects and Altered MAP-kinase Signaling" PLOS Genetics (DOI:10.1371/journal.pgen.1005684) pp. 1-21 2015.
Neiman, A. "Sporulation in the Budding Yeast *Saccharomyces cerevisiae*" Genetics, 189:737-765 2011.

(Continued)

*Primary Examiner* — Sarvamangala Devi
(74) *Attorney, Agent, or Firm* — Myers Bigel, P.A.

(57) ABSTRACT

The invention is directed to methods for identifying targets for antimicrobial and antiproliferative compounds as well as methods for identifying novel compounds for treating cancer and microbial infections.

5 Claims, 3 Drawing Sheets

(56) References Cited

OTHER PUBLICATIONS

Orlowski, M. "Mucor Dimorphism" Microbiological Reviews, 55:234-258 1991.
Yu, JH. "Regulation of Development in Aspergillus nidulans and Aspergillus fumigatus" Mycobiology, 38(4):229-237 2010.
Brauer MJ et al. Coordination of growth rate, cell cycle, stress response, and metabolic activity in yeast. Molecular Biology of the Cell. Jan. 2008; 19: 352-367.
Canepa A et al. Free amino acids in plasma, red blood cells, polymorphnuclear leukocytes, and muscle in normal and uraemic children. Nephrology and Dialysis Transplantation. 2002; 17: 413-421.
Creanor J. Carbon dioxide evolution during the cell cycle of the fission yeast *Schizosaccharomyces pombe*. J Cell Sci. 1978; 33: 385-397.
Cuenca-Estrella M et al.Comparison of the Vitek 2 antifungal susceptibility system with the Clinical and Laboratory Standards Institute (CLSI) and European Committee on Antimicrobial Susceptibility Testing (EUCAST)broth microdilution reference methods and with the Sensititre YeastOne and Etest techiques for in vitro detection of antifungal resistance in yeast isolates. Journal of Clinical Microbiology. May 2010; 48(5): 1782-1786.
Fothergill AW et al. Antifungal susceptibility testing. Infectious Disease Clinics of North America. 2006; 20: 699-709.
Futcher B. Metabolic cycle, cell cycle, and the finishing kick to Start. Genome Biology. Apr. 2006; 7(4), Article 107: 107, 5 pages.
Gasch AP et al. Genomic expression programs in the response of yeast cells to environmental changes. Molecular Biology of the Cell. Dec. 2000; 11: 4241-4257.
Gethin G. The significance of surface pH in chronic wounds. Wounds UK. 2007; 3(3): 52-56.
Guirao-Aban JP et al. Analysis of validamycin as a potential antifungal compounds against Candida albicans. International Microbiology. 2013; 16: 217-225.
Haase SB and Wittenberg C. Topology and control of the cell-cycle-regulated transcriptional circuitry. Genetics. Jan. 2014; 196: 65-90.
Klevecz RR et al. A genomewide oscillation in transcription gates DNA replication and cell cycle. PNAS. Feb. 2004; 101(5): 1200-1205.
Luft FC et al. Infections or neoplasm as causes of prolonged fever in cancer patients. American Journal of the Medical Sciences. Jul.-Aug. 1976; 272(1): 65-74.
Madhani HD and Fink GR. The control of filamentous differentiation and virulence in fungi. Trends in Cell Biology. Sep. 1998; 8: 348-353.
Mandal R et al. Multi-platform characterization of the human cerebrospinal fluid metabolome: a comprehensive and quantitative update. Genome Medicine. 2012; 4: 38, 11 pages.
Merril CR et al. Total CO2, Pco2, and pH in human spinal fluid. J Apppl Phisiol. 1961; 16(3): 485-487.
Nobre A et al. The molecular biology of mycobacterial trehalose in the quest for advanced tuberculosis therapies. Microbiology. 2014; 160: 1547-1570.
Novak B and Mitchison JM. Changes in the rate of oxygen consumption in synchronous cultures of the fission yeast *Schizosaccharomyces pombe*. Journal of Cell Sciences. 1990; 96: 429-433.
Novak B and Mitchison. Change in the rate of CO2 production in synchronous cultures of the fission yeast *Schizosaccharomyces pombe*: a periodic cell cycle event that persists after the DNA-division cycle has been blocked. Journal of Cell Sciences. 1986; 86: 191-206.
Onitilo AA et al. Tumor-related hyponatremia. Clinical Medicine & Research. Dec. 2007; 5(4): 228-237.
Peng LH et al. Fever in children with acute lymphoblastic leukemia. Cancer. 1981; 47: 583-587.
Petzold EW et al. Characterization and regulation of the trehalose synthesis pathway and its importance in the pathogenicity of Cryptococcus neoformans. Infection and Immunity. Oct. 2006; 74(10): 5877-5887.
Rubin-Bejerano I et al. Phagocytosis by human neutrophils is stimulated by a unique fungal cell wall component. Cell Host & Microbe. Jul. 2007; 2: 55-67.
Slavov N and Botstein D. Coupling among growth rate response, metabolic cycle, and cell division cycle in yeast. Molecular Biology of the Cell. Jun. 2011; 22: 1997-2009.
Tannock IF and Rotin D. Acid pH in tumors and its potential for therapeutic exploitation. Cancer Research. Aug. 1989; 49: 4373-4384.
Tu BP et al. Logic of the yeast metabolic cycle: temporal compartmentalization of cellular processes. Science. Nov. 2005; 310: 1152-1158. Erratum post date Feb. 2006, 1 page.
Walenta S et al. High lactate levels predict likelihood of metastases, tumor recurrence, and restricted patient survival in human cervical cancers. Cancer Research. Feb. 2000; 60: 916-921.
Isikawa R et al. Antibacterial activity of validamysin A against Pseudomonas solanacearum and its efficacy against tomato bacterial wilt. Annals of the Phytopathological Society of Japan. Jan. 1996; 62(5): 478-482.
Crabbe A et al. Mimicking the host and its microenvironment in vitro for studying mucosal infections by Pseudomonas aeruginosa. Pathogens and disease. May 2014; 71(1): 1-19.
Cooksey RC et al. Characterization of Mycobacterium tuberculosis complex isolates from the cerebrospinal fluid of meningitis patients at six fever hospitals in Egypt. Journal of Clinical Microbiology. May 2002; 40(5): 1651-1655.
Barrila J et al. Organotypic 3D cell culture models: using the rotating wall vessel to study host-pathogen interactions. Nature Reviews Microbiology. Nov. 2010; 8(11): 791-801.
Supplementary European Search Report, EP 16793387.8, dated Jan. 18, 2019, 10 pages.

* cited by examiner

METHODS FOR IDENTIFYING TARGETS FOR ANTIMICROBIAL AND ANTIPROLIFERATIVE COMPOUNDS AND COMPOSITIONS THEREFROM

STATEMENT OF PRIORITY

This application is a 35 U.S.C. § 371 national phase application of International Application Serial No. PCT/US2016/031712, filed May 11, 2016, which claims the benefit, under 35 U.S.C. § 119 (a) of U.S. Patent Application No. 62/179,545, filed May 11, 2015, the entire contents of each of which are incorporated by reference herein.

RELATED APPLICATIONS

This application claims the benefit of U.S. Provisional Application No. 62/179,545, filed May 11, 2015. The entire content of this application is fully incorporated herein by reference.

FIELD OF THE INVENTION

The invention relates to methods for identifying targets for antimicrobial and antiproliferative compounds as well as methods for identifying novel compounds for treating microbial infections and cancer.

BACKGROUND OF THE INVENTION

There are a variety of approaches for discovering antimicrobial or antiproliferative compounds that range from identifying specific drug targets and then designing chemical agents to attack these targets (so-called 'rational' drug design), or by pharmacological screening of libraries of chemical compounds that have a desired chemotherapeutic effect (e.g., antimicrobials that kill a specific disease causing organism). Whether screening genetic pathways for novel drug targets, or screening compound libraries for pharmacological activity, the initial screening conditions constrain the targets or compounds to a smaller subset that will be analyzed further. For reasons of safety and practicality these initial screening steps are always performed in vitro. Successfully identifying potential compounds during the primary in vitro screening process is critical, as any putative drug or drug target that does not make it through this screen will not be evaluated further in an in vivo system.

The present invention overcomes previous shortcomings in the art by providing novel methods for identifying targets for antimicrobial and antiproliferative compounds as well as methods for identifying novel compounds for treating cancer and microbial infections.

SUMMARY OF THE INVENTION

One aspect of the invention provides a method of identifying one or more antimicrobial molecular targets in a fungal cell and/or bacterial cell, comprising: growing the fungal cell and/or bacterial cell in vitro under infection mimetic conditions; identifying genes that are differentially regulated (i.e., upregulated or downregulated) in the fungal cell and/or bacterial cell when grown under infection mimetic conditions as compared to the fungal cell and/or bacterial cell grown in vitro under standard or clinical laboratory conditions.

A second aspect of the invention provides a method of identifying a compound having antimicrobial activity, comprising: growing a microbe in vitro under infection mimetic conditions in the presence or absence of a test compound; and selecting a compound that reduces the growth of or kills the microbe as compared to the microbe grown in vitro under infection mimetic conditions in the absence of the compound.

A third aspect of the invention provides a method of identifying a compound having antimicrobial activity against a microbe in a clinical sample, comprising; culturing the clinical sample or a portion of the clinical sample in vitro under conditions that mimic an infection site in the presence or absence of a test compound; selecting a compound that reduces the growth of or kills the microbe in the clinical sample as compared to the microbe grown in vitro under infection mimetic conditions in the absence of the compound.

A fourth aspect of the invention provides a method of treating a fungal infection in an organism, comprising administering to an organism in need thereof a therapeutically effective amount of validamycin A.

A fifth aspect of the invention provides a media that mimics conditions at an infection site in an organism.

A sixth aspect of the invention provides a method of identifying one or more antiproliferative molecular targets in a mammalian cancer cell, comprising: growing the mammalian cancer cell in vitro under cancer mimetic conditions; identifying genes that are upregulated in the mammalian cancer cell when grown under cancer mimetic conditions as compared to the mammalian cancer cell grown in vitro under standard or clinical laboratory conditions.

A seventh aspect of the invention provides a method of identifying a compound having antiproliferative activity, comprising: growing a mammalian cancer cell in vitro under cancer mimetic conditions in the presence or absence of a test compound; and selecting a compound that reduces the growth of or kills the mammalian cancer cell as compared to the mammalian cancer cell grown in vitro under cancer mimetic conditions in the absence of the compound.

An eighth aspect of the invention provides a method of identifying a compound having antiproliferative activity against a mammalian cancer cell in a clinical sample, comprising: culturing the clinical sample or a portion of the clinical sample in vitro under conditions that mimic a site of cancer proliferation in the presence or absence of a test compound; and selecting a compound that reduces the growth of or kills the mammalian cancer cell in the clinical sample as compared to the mammalian cancer cell grown in vitro under cancer mimetic conditions in the absence of the compound.

A ninth aspect of the invention provides a cancer mimetic media that mimics conditions at a site of cancer growth in a mammal.

These and other aspects of the invention are set forth in more detail in the description of the invention below.

DETAILED DESCRIPTION

Figure 1:
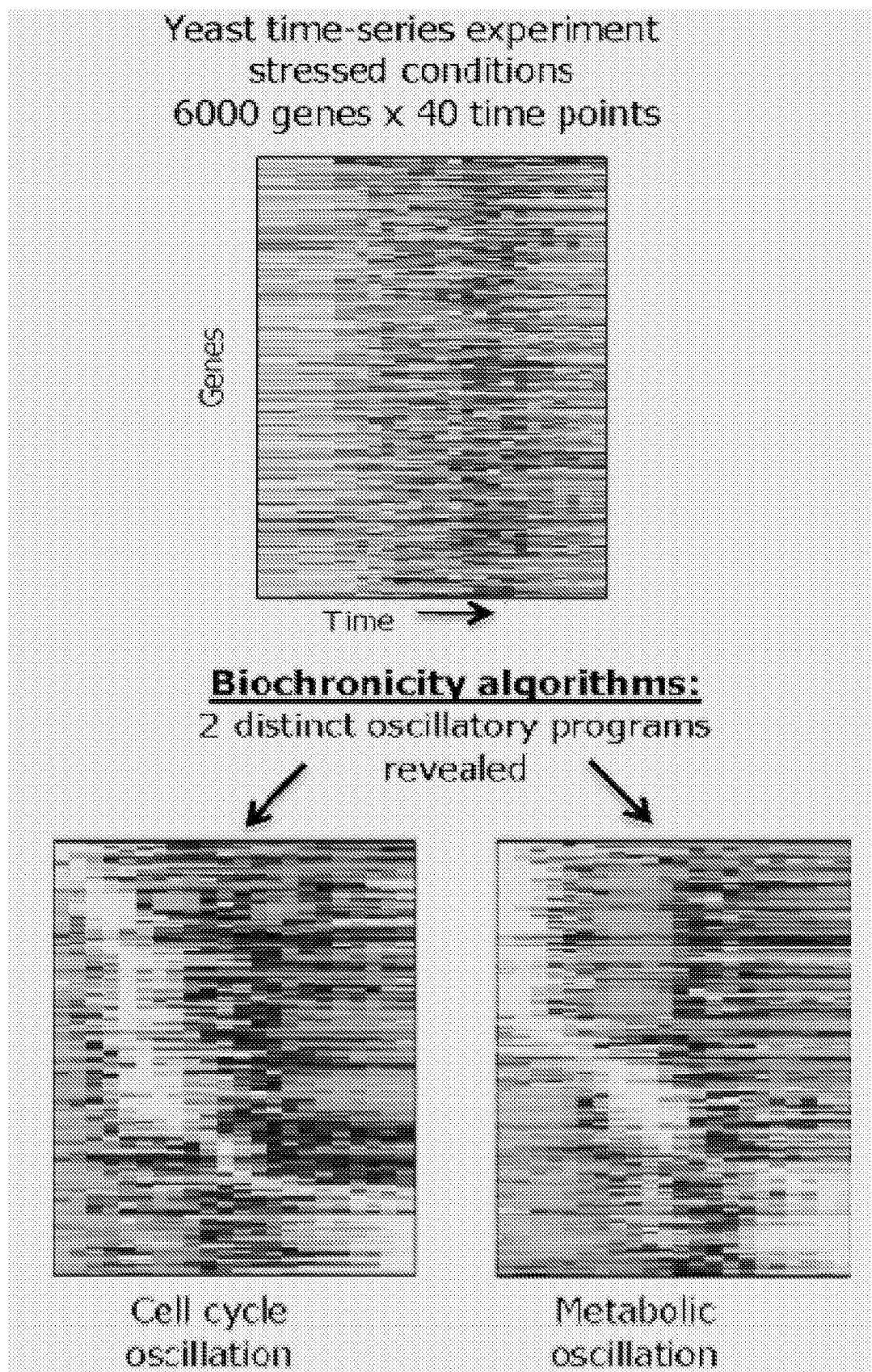
FIG. 1 provides evidence of a new program of gene expression in slow growth. Budding yeast mutant (rho$^0$) cells were synchronized in early G1 and released into the cell cycle. Genome-wide transcript levels were determined at multiple time points as cells progressing through the cell cycle by microarray analysis. Algorithms were used to identify periodic transcripts and the transcript profiles are shown by heat map. Data are expressed as logfold change/mean. White represents above the mean of expression, Gray represents below mean expression. Rho$^0$ mutant cells exhibit the normal cell cycle transcription program, as well as a new program of expression that heavily overlaps with the yeast metabolic cycle. The yeast metabolic cycle (YMC) program is not observed in wild-type cells growing in optimized conditions.

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like refers to variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the terms "increase," "increasing," "increased," "enhance," "enhanced," "enhancing," and "enhancement" (and grammatical variations thereof) describe an elevation of at least about 25%, 50%, 75%, 100%, 150%, 200%, 300%, 400%, 500% or more as compared to a control.

As used herein, the terms "reduce," "reduced," "reducing," "reduction," "diminish," and "decrease" (and grammatical variations thereof), describe, for example, a decrease of at least about 5%, 10%, 15%, 20%, 25%, 35%, 50%, 75%, 80%, 85%, 90%, 95%, 97%, 98%, 99%, or 100% as compared to a control. In particular embodiments, the reduction can result in no or essentially no (i.e., an insignificant amount, e.g., less than about 10% or even 5%) detectable activity or amount.

An "antimicrobial molecular target" as used herein means a molecular target (nucleic acid, polypeptide) for an antimicrobial compound.

As used herein, "infection mimetic conditions" are conditions designed to mimic those found in or on an infected host (e.g., an animal, a plant) such as, for example, conditions of low nutrient, high/low temperature, high/low osmotic potential (high/low salt); high/low humidity, high/low pH, high/low oxygen and that do not support an optimal rate of cell division for any given fungal cell or bacterial cell; that is, conditions that mimic conditions encountered by the organism during infection. Such conditions are well known in the art. Each parameter for an infection mimetic condition is identical to or is within at least about 20% (e.g., about 20%, 19%, 18%, 17%, 16%, 15%, 14%, 13%, 12%, 11%, 10%, 9%, 8%, 7%, 6%, 5%, 4%, 3%, 2%, 1%) of the same parameter at a given infection site. Infection mimetic conditions are thus suboptimal conditions when compared to the optimal laboratory conditions provided for growth of fungal cells and/or bacterial cells. Infection mimetic conditions include variance in any of the conditions noted above, e.g., variance in temperature as experienced by an organism during daylight/nighttime hours. In some aspects, infection mimetic conditions can be any conditions in which the fungal cell or bacterial cell grows at a lower rate than it grows when placed under standard laboratory conditions that are generally developed to optimize cell growth rate to increase rapidity of experimental/analytical processes. Thus, in some aspects, the infection mimetic conditions provide growth rates for a bacterium or a fungus that are reduced by at least about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86, 87%, 88%, 89%, 90%, 91%, 92%, 93%, 94%, 95%, 96%, 97%, 98%, 99%, or 100%, or any range or value therein, as compared to growth of the same bacterium or fungus grown under standard laboratory or clinical conditions.

As used herein, "antiproliferative molecular target" means a molecular target (nucleic acid, polypeptide) for an antiproliferative compound.

As used herein, "cancer mimetic conditions" means conditions designed to mimic those found at the site of cancer proliferation in a mammal including but not limited to conditions of low nutrient, limited growth factors, high/low temperature, high/low osmotic potential (high/low salt), high/low humidity, high/low pH, high/low oxygen, increased lactate, altered extracellular matrix, and that do not support an optimal rate of cell division for any given mammalian cancer cell; that is, conditions that mimic conditions encountered by the cancer cell during proliferation. Cancer mimetic conditions are thus suboptimal conditions when compared to the optimal laboratory conditions provided for growth of mammalian cancer cells. These conditions are well known in the art and include the tumor microenvironment and/or the intratumoral environment for solid tumors and circulating blood for blood cell cancers. Each parameter for a cancer mimetic condition is identical to or is within at least about 20% (e.g., about 20%, 19%, 18%, 17%, 16%, 15%, 14%, 13%, 12%, 11%, 10%, 9%, 8%, 7%, 6%, 5%, 4%, 3%, 2%, 1%) of the same parameter at a given site of cancer proliferation. In some aspects, cancer mimetic conditions can be any conditions in which a cancer cell grows at a lower rate than it grows when placed under standard laboratory conditions that are generally developed to optimize cell growth rate to increase rapidity of experimental/analytical processes. Thus, in some aspects, the cancer mimetic conditions provide growth rates for cancer cells that are reduced by at least about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86, 87%, 88%, 89%, 90%, 91%, 92%, 93%, 94%, 95%, 96%, 97%, 98%, 99%, or 100%, or any range or value therein, as compared to growth of the same cancer cells grown under standard laboratory or clinical conditions.

As used herein, "standard laboratory conditions" or "clinical laboratory conditions" are conditions designed to optimize the growth and cell division of an organism or a cancer cell by providing optimal nutrients, temperature, pH, osmotic potential, oxygen, water/humidity; that is, the conditions that provide the optimal rate of cell division and growth for any given fungal cell, bacterial cell or cultured mammalian cancer cell. "Optimized growth conditions" are those used for culture of organisms in a laboratory setting. Conditions are generally developed to optimize cell growth rate to increase rapidity of experimental/analytical processes. While conditions used may not provide the environment for maximal growth rates, they are substantially more favorable than conditions encountered by the cell during growth in the infection mimetic environment The present invention is directed in part to novel methods for screening compounds for antimicrobial and antiproliferative activity. The assumption underlying prior known standard screening processes and protocols is that a finding that compounds that fail to exhibit activity against pathogens in these in vitro environments is conclusive as to whether the same molecules will show activity in vivo. The question of whether this assumption is justified or not has rarely been posed, let alone carefully investigated. Although standard approaches based on this assumption have successfully identified a variety of anti-microbial and anti-proliferative drugs, it is clear from our recent research findings that a variety of important drugs and drug targets are missed in primary screens.

Primary (in vitro) screening protocols are usually optimized to identify drugs or drug targets rapidly and at minimum cost. This generally involves growing organisms in conditions that are optimized for the growth of the pathogen of interest. For example, to screen for antibacterial activity, disease-causing bacteria are grown in a rich medium that supports rapid growth, and then exposed to the potential antibiotic on either solid or liquid media. Cells are then incubated at optimal growth temperatures so that growth-inhibiting properties can be scored rapidly. Protocols of this type have also been standardized for assessing antibiotic sensitivity in clinical settings, so that the proper antibiotic can be used to treat an infection [1]. A further benefit of standardized protocols is the ability to directly compare the relative efficacy of various drugs while holding the environmental conditions constant.

The central issue facing current standardized screening methods is that the growth conditions are optimized for rapid growth, and these optimized growth conditions are far from what are encountered by pathogenic organisms living in a host. For example, infected tissues do not provide the pathogen with the high levels of sugars (e.g. 2% w/v/ dextrose), proteins, and micronutrients available in the rich media formulas used for in vitro growth. Moreover, pathogens are likely to encounter additional stresses such as high temperatures, due to fever, a dynamic osmotic environment, as well as attacks from the immune system. The first indication of the importance of distinguishing between growth conditions in the infected host and in vitro lab test conditions can be seen in the decades of studies and observations indicating that cell growth and division are substantially altered in low nutrient or stressful conditions. This suggests that the response of pathogenic organisms to antimicrobial compounds may be very different when they are grown under optimized growth conditions rather than in nutrient-limited or stressful conditions such as that of infection conditions.

Several studies demonstrate how fungal cells (S. cerevisiae) respond differently to optimized growth conditions vs. nutrient depleted conditions [2]. Gene expression programs are markedly different when cells are dividing slowly in media depleted for a variety of nutrients. Interestingly, the GRR (Growth Rate Regulated) response (the profile of differentially expressed genes (i.e., up-regulated or down-regulated) is very similar, regardless of which nutrient is depleted [2]. Moreover, the set of GRR genes was found to substantially overlap with a set of ESR (Environmental Stress Response) that are differentially expressed in response to a variety of stresses (e.g. osmotic stress) [3,4]. Genes that exhibited positive correlation with growth rate tended to be genes inhibited by stress, while genes that were down-regulated in fast growth conditions were often activated by stress [2]. As well, considerable overlap was observed between the GRR gene set and the Yeast Metabolic Cycle responsive gene sets identified by Tu et al. [2,5]. Thus, these yeast cells appear to mount a similar gene expression response to either low nutrients (GRR) or a variety of stresses (Stress Response Genes) that is disjoint from the gene expression program observed in cells dividing rapidly in optimized growth conditions.

Studies that employed a chemostat in which the growth/ division rate of cells can be precisely controlled revealed that the gene expression patterns of the GRR are dynamic, and oscillate in a program referred to as the Yeast Metabolic Cycle (YMC). It has been recognized for some time that metabolic processes in yeast are periodically regulated [6] and may be coordinated with the cell cycle [7-9]. When budding yeast cells are grown in continuous culture conditions (chemostat) at appropriate densities and growth rates, the cells synchronize in robust metabolic cycles that can be monitored by periodic changes in dissolved oxygen.

By sampling continuous cultures of metabolically synchronous populations of budding yeast over time, oscillations in gene expression are identified that are coincident with the periodicity of the YMC. The reported periods of the YMC can vary substantially [4,5,10], and seem to be linked to growth rate [2,4]. The YMC regulates a large transcriptional program and appears to be coordinated with the cell cycle under slow growth conditions. Under continuous culture conditions and a variety of nutritional limitations, researchers demonstrated that all of the GRR transcripts were, in fact, periodic during the YMC [4]. Taken together, these findings suggest that the mechanisms controlling oscillation in transcript abundance are integrating signals from stress, growth rate, YMC and cell cycle.

The salient question is whether this dynamic program of gene expression in response to nutrient limitation and stress is simply a response to nutrient limitation or stress, or whether its execution is essential for continued growth and division under these slow growth conditions. Those genes that may be important for growth under these conditions of nutrient limitation and stress, once identified may be useful as targets for antimicrobial compounds.

Accordingly, a first aspect of the invention provides a method of identifying one or more antimicrobial molecular targets in a fungal cell and/or bacterial cell, comprising: growing the fungal cell and/or bacterial cell in vitro under infection mimetic conditions; identifying genes that are differentially expressed (i.e., upregulated or downregulated) in the fungal cell and/or bacterial cell when grown under infection mimetic conditions as compared to the fungal cell and/or bacterial cell grown in vitro under standard or clinical laboratory conditions. In some embodiments, the growth conditions can mimic conditions at a site of an infection by a fungal or bacterial cell (i.e., infection mimetic conditions).

A second aspect of the invention provides a method of identifying a compound having antimicrobial activity, comprising: growing a microbe (e.g., bacterium or fungus) in vitro under infection mimetic conditions in the presence or absence of a test compound; and selecting a compound that reduces the growth of (e.g., reduces the rate of cell division) or kills the microbe as compared to the microbe grown in vitro under infection mimetic conditions in the absence of the compound.

A third aspect of the invention provides a method of identifying a compound having antimicrobial activity against a microbe (i.e., bacterium or fungus) in a clinical sample, comprising culturing the clinical sample or a portion of the clinical sample in vitro under conditions that mimic an infection site in the presence or absence of a test compound; selecting a compound that reduces the growth of (e.g., reduces the rate of cell division) or kills the microbe in the clinical sample as compared to the microbe grown in vitro under infection mimetic conditions in the absence of the compound. In some embodiments, the infection site can be where the clinical sample was obtained or the clinical sample can be obtained from a different site. Microbes are bacteria and/or fungi as described herein.

A clinical sample can be prepared by removing a portion of tissue from a patient/subject and culturing the portion of tissue or other sample on a plate or in a dish in an infection mimetic medium, wherein the growth conditions provided by the infection mimetic media (e.g., temperature, pH, nutrients, etc) mimic those in the infected host organism, for example at the site of infection in the infected organism.

A clinical sample may be obtained by any method known in the art, such as surgery, biopsy, lavage, aspiration, etc. The sample may be a bodily fluid, e.g., blood, serum, plasma, saliva, urine, cerebrospinal fluid, perspiration, etc.

As used herein, upregulation of a gene means an increase in expression (i.e., mRNA levels) by that gene of at least about 5% to about 500% or more as compared to a control (e.g., expression levels of the same gene when not grown under infection mimetic or cancer mimetic conditions). Thus, in some embodiments, upregulation of a gene means an increase in mRNA levels of at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86, 87%, 88%, 89%, 90%, 91%, 92%, 93%, 94%, 95%, 96%, 97%, 98%, 99%, 100%, 105%, 110%, 115%, 120%, 125%, 130%, 135%, 140%, 145%, 150%, 155%, 160%, 165%, 170%, 175%, 180%, 185%, 190%, 195%, 200%, 205%, 210%, 215%, 220%, 225%, 230%, 235%, 240%, 245%, 250%, 255%, 260%, 265%, 270%, 275%, 280%, 285%, 290%, 295%, 300%, 305%, 310%, 315%, 320%, 325%, 330%, 335%, 340%, 145%, 350%, 355%, 360%, 365%, 370%, 375%, 380%, 385%, 390%, 395%, 400%, 405%, 410%, 415%, 420%, 425%, 430%, 435%, 440%, 445%, 450%, 455%, 460%, 465%, 470%, 475%, 480%, 485%, 490%, 495%, 500%, or any value or range therein. In some embodiments, upregulation of a gene means an increase in mRNA levels of at least about 10% to about 500%, about 10% to about 450%, about 10% to about 400%, about 10% to about 350%, about 10% to about 300%, about 10% to about 250%, about 10% to about 200%, about 10% to about 100%, about 10% to about 90%, about 10% to about 80%, about 20% to about 500%, about 20% to about 450%, about 20% to about 400%, about 20% to about 350%, about 20% to about 300%, about 20% to about 250%, about 20% to about 200%, about 20% to about 100%, about 20% to about 90%, about 20% to about 80%, about 20% to about 60%, about 30% to about 500%, about 30% to about 450%, about 30% to about 400%, about 30% to about 350%, about 30% to about 300%, about 30% to about 250%, about 30% to about 200%, about 30% to about 100%, about 30% to about 90%, about 30% to about 80%, about 30% to about 60%, about 50% to about 500%, about 50% to about 450%, about 50% to about 400%, about 50% to about 350%, about 50% to about 300%, about 50% to about 250%, about 50% to about 200%, about 50% to about 100%, about 50% to about 90%, about 50% to about 80%, about 100% to about 500%, about 100% to about 400%, about 100% to about 300%, and the like. The level of upregulation or increase in mRNA expression can vary depending on the organism and/or the particular gene.

As used herein, down-regulation of a gene means a decrease in expression (i.e., mRNA levels) by that gene of at least about 5% to about 100% compared to a control (e.g., expression levels of the same gene when not grown under infection mimetic or cancer mimetic conditions). Thus, in some embodiments, downregulation of a gene means a decrease in mRNA levels of at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86, 87%, 88%, 89%, 90%, 91%, 92%, 93%, 94%, 95%, 96%, 97%, 98%, 99%, 100%, or any value or range therein. In some embodiments, downregulation of a gene means a decrease in mRNA levels of at least about 10% to about 100%, about 10% to about 90%, about 10% to about 80%, about 10% to about 70%, about 10% to about 60%, about 15% to about 100%, about 15% to about 90%, about 15% to about 80%, about 15% to about 70%, about 15% to about 60%, about 20% to about 100%, about 20% to about 90%, about 20% to about 80%, about 20% to about 70%, about 20% to about 60%, about 30% to about 100%, about 30% to about 90%, about 30% to about 80%, about 30% to about 70%, about 30% to about 60%, about 40% to about 100%, about 50% to about 100%, and the like. The level of downregulation or decrease in mRNA expression can vary depending on the organism and/or the particular gene.

In some embodiments, a compound can reduce the growth or the rate of cell division of the organism by at least about 5% to about 100% as compared to a control. Thus, in some embodiments, the growth or the rate of cell division of an organism can be reduced by at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86, 87%, 88%, 89%, 90%, 91%, 92%, 93%, 94%, 95%, 96%, 97%, 98%, 99%, 100%, or any value or range therein. In representative embodiments, the rate of growth or the rate of cell division of an organism can be reduced by at least about 10% to about 100%, about 10% to about 90%, about 10% to about 80%, about 10% to about 70%, about 10% to about 60%, about 15% to about 100%, about 150% to about 90%, about 15% to about 80%, about 15% to about 70%, about 15% to about 60%, about 20% to about 100%, about 20% to about 90%, about 20% to about 80%, about 20% to about 70%, about 20% to about 60%, about 30% to about 100%, about 30% to about 90%, about 30% to about 80%, about 30% to about 70%, about 30% to about 60%, about 40% to about 100%, about 50% to about 100%, and the like. The reduction in growth can vary depending on the organism and/or the compound being tested.

In some embodiments, the site of infection can be in an animal, optionally a mammal, an avian, a reptile, a fish, an amphibian, or an insect. As used herein, a mammal can include but is not limited to a human, non-human primate (e.g., gorilla, monkey, baboon, and chimpanzee, etc.), dog, cat, goat, horse, pig, cow, sheep, and the like, or a laboratory animal (e.g., rats, guinea pigs, mice, gerbils, hamsters, and the like). As used herein, an avian can include but is not limited to a chicken, duck, turkey, goose, quail, pheasant, or a bird kept as a pet (e.g., parakeets, parrots, macaws, cockatoos, canaries, and the like). Both male and female animals and animals of any age are suitable, including embryonic (e.g., in utero or in ovo), infant, juvenile, adolescent, adult and geriatric animals. In representative embodiments, the site of infection can be in a mammal, optionally a human.

In some embodiments, the site of infection can be in a mammal and the infection mimetic conditions can mimic, for example, cerebral spinal fluid, blood, epidermal surface, mucosal surface (eye, mouth, intestine, genital tract, nasal tract), lung surface, brain tissue, bladder, kidney, a wound, and/or other organ or tissue. These conditions are well known in the art and infection mimetic media can be readily developed to mimic these conditions.

Exemplary conditions that mimic fungal meningitis infection in cerebral spinal fluid can include normal sodium levels, increased temperature (e.g., fever), low carbohydrate, elevated pH, and low nitrogen and exemplary conditions mimicking a microbial wound site can include low sodium levels, elevated temperature, elevated pH and low nitrogen.

Exemplary cancer mimetic mimetic conditions for media of this invention are provided in Table 1.

TABLE 1

Exemplary infection mimetic conditions

| Mimetic Condition | Microbial Blood Infection | Fungal Meningitis (Cerebral Spinal Fluid) | Microbial Wound Infection |
|---|---|---|---|
| Salt Content | 150 mM NaCl | 150 mM NaCl | Low NaCl (<150 mM) |
| Temperature | >37° C. [18] | >37° C. [18] | >37° C. [18] |
| Oxygen levels | Normoxic | Normoxic | Hypoxic |
| pH | <7.35 | ~7.35 [20] | 7.15-8.9 [21] |
| Carbohydrate Content | Glucose 5.5 mM | Glucose 3 mM [23] | Glucose 5.5 mM |
| Nitrogen Content | Free Amino Acids [24] | Urea 4 mM [23] | Free Amino Acids [24] |
| Extracellular Matrix | None | None | Collagen Elastin Fibronectin |
| Other cell types in co-culture | Macrophages [25] Neutrophils [26] | No | Macrophages [25] Neutrophils [26] |
| Hormones or Cytokines | Human Serum Factors [27] | No | Interleukin-1 Tumor Necrosis Factor [25] |

In some aspects, infection mimetic conditions can be any conditions in which the fungal cell or bacterial cell grows or divides at a lower rate than when placed under standard laboratory conditions that are generally developed to optimize cell growth rate to increase rapidity of experimental/analytical processes. An exemplary medium designed for reduced growth and reduced cell division in a bacterium or a fungus includes, for example, a medium comprising Yeast Nitrogen Base supplemented with essential amino acids and either 3% (v/v) Glycerol/3% (v/v) Ethanol or 3% Ethanol (v/v) only.

A fungal cell or a bacterial cell can be from any fungal genera or bacterial genera that can cause disease and infection (i.e., pathogenic) in an animal (e.g., in a mammal, an avian, a reptile, a fish, an amphibian, or an insect). Non-limiting examples of bacterial pathogens include *Bacillus* spp., *Bordetella* spp., *Brucella* spp., *Borrellia* spp., *Campylobacter* spp., *Chlamydia* spp., *Clostridium* spp., *Corynebacterium* spp., *Enteroccocus* spp., *Escherichia* spp., *Haemophilus* spp., *Helicobacter* spp., *Legionella* spp., *Leptospira* spp., *Listeria* spp., *Mycobacterium* spp., *Mycoplasma* spp., *Neisseria* spp., *Psuedomonas* spp., *Rickettsia* spp., *Salmonella* spp., *Shigella* spp., *Staphylococcus* spp., *Streptococcus* spp., *Vibrio* spp., or *Yersinia* spp. Examples of bacterial species useful with this invention include, but are not limited to, *Bacillus anthracis, Bacillus cereus, Bordetella pertussis, Brucella abortus, Brucella canis, Brucella melitensis, Borrelia burgdorferi, Borrelia garinii, Borrelia afzelii, Borrelia recurrentis, Campylobacter jejuni, Chlamydia pneumoniae, Chlamydia trachomatis, Clostridium botulinum, Clostridium difficile, Clostridium perfringens, Clostridium tetani, Corynebacterium diphtheriae, Enteroccocus faecalis, Enteroccocus faecium, Escherichia coli, Haemophilus influenzae, Helicobacter pylori, Legionella pneumophila, Leptospira interrogans, Leptospira santarosai, Leptospira weilii, Leptospira noguchii, Listeria monocytogenes, Mycobacterium leprae, Mycobacterium tuberculosis, Mycobacterium ulcerans, Mycoplasma pneumoniae, Neisseria gonorrhoeae, Neisseria meningitidis, Psuedomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyrogenes, Vibrio cholerae,* or *Yersinia pestis, Yersinia enterocolitica* or *Yersinia pseudotuberculosis.* In representative embodiments, the bacterial cell can be a cell from the genera of, for example, *Mycobacterium* spp., optionally, *Mycobacterium tuberculosis*.

Non-limiting examples of an animal fungal pathogen include *Cryptococcus* spp., *Candida* spp., *Mucor* spp., *Aspergillus* spp., *Histoplasma* spp, *Pneumocytis* spp., or *Stachybotrys* spp. Examples of fungal species useful with this invention include, but are not limited to, *Cryptococcus neoformans, Candida albicans, Candida tropicalis, Mucor circinelloides, Aspergillus fumigatus Histoplasma capsulatum, Pneumocytis jirovecii, Trichophyton* spp., *Epidermophyton* spp., *Microsporum* spp, or *Tinea* spp. or *Stachybotrys chartarum.* In representative embodiments, the fungal cell can be a cell from *Cryptococcus neoformans, Candida albicans, Candida tropicalis, Mucor circinelloides,* and/or *Aspergillus fumigatus.*

In representative embodiments, the site of infection can be in a mammal and infection mimetic conditions can mimic cerebral spinal fluid. In some embodiments, a method of identifying one or more antimicrobial molecular targets in a fungal cell or a bacterial cell is provided, comprising: growing the fungal cell or bacterial cell in vitro under infection mimetic conditions that mimic cerebral spinal fluid; identifying genes that are differentially regulated in the fungal cell or bacterial cell when grown under infection mimetic conditions as compared to the fungal cell or bacterial cell grown in vitro under standard or clinical laboratory conditions, wherein the conditions that mimic cerebral spinal fluid comprise a medium comprising phosphate buffered saline (PBS), urea (5 g/L) and 0.1% (w/v) dextrose. In some embodiments, the fungal cell can be *Cryptococcus* spp., optionally *Cryptococcus neoformans*. In some embodiments, the standard laboratory conditions that support rapid cell division can comprise a media comprising yeast extract peptone dextrose (YEPD) with 2% (w/v) dextrose.

In further embodiments, a method of identifying a compound having antimicrobial activity is provided, comprising: growing a fungus or bacterium in vitro under infection mimetic conditions that mimic cerebral spinal fluid in the presence or absence of a test compound; and selecting a compound that reduces the growth of or kills the fungus or bacterium as compared to the fungus or bacterium grown in vitro under infection mimetic conditions in the absence of the compound, wherein the conditions that mimic cerebral spinal fluid comprise a medium comprising phosphate buffered saline (PBS), urea (5 g/L) and 0.1% (w/v) dextrose. In some embodiments, the fungal cell is *Cryptococcus* spp., optionally *Cryptococcus neoformans*.

In still further embodiments, a method of identifying a compound having antimicrobial activity against a fungus or a bacterium in a clinical sample is provided, comprising culturing the clinical sample or a portion of the clinical sample in vitro under conditions that mimic an infection site in the presence or absence of a test compound, wherein the conditions that mimic an infection site mimic cerebral spinal fluid; selecting a compound that reduces the growth of or kills the fungus or a bacterium in the clinical sample as compared to the fungus or a bacterium grown in vitro under infection mimetic conditions in the absence of the compound, wherein the conditions that mimic cerebral spinal fluid can comprise low nitrogen and low carbohydrate. Thus, for example, a condition that mimics cerebral spinal fluid can comprise a medium comprising phosphate buffered saline (PBS), urea (5 g/L) and 0.1% (w/v) dextrose. In some embodiments, the fungal cell can be *Cryptococcus* spp., optionally *Cryptococcus neoformans*. In some embodiments, the infection site can be where the clinical sample was obtained or the clinical sample can be obtained from a different site.

Exemplary optimal growth media for budding yeast and other microbes can include, but is not limited to, (1) YEP medium comprising 10 g yeast extract, 10 g Bacto peptone, 5 g NaCl in a total volume of 1 L of water, pH to 7.0) and 2% (w/v) dextrose; (2) yeast nitrogen base (YNB) medium supplemented with essential amino acids, 2% (w/v) dextrose and either: (i) 3% glycerol/3% ethanol (v/v) or (ii) 3% ethanol (v/v); (3) yeast extract peptone dextrose (YEPD) medium comprising yeast extract peptone dextrose and 2% (w/v) dextrose.

In further embodiments, the site of infection can be in or on a plant and the infection mimetic conditions can mimic conditions on a plant surface (leaf, stem, flower, root, fruit), in phloem, in xylem, or within and/or between a plant's cells (i.e., intracellular and/or intercellular), and/or in or on other plant tissue types. In still further embodiments, the site of infection can be in or on a plant and the infection mimetic conditions can mimic conditions in the soil. The conditions on a plant surface (e.g., leaf surface, stem surface, petal surface, and the like) at the time of bacterial or fungal infection can be the conditions at the site of infection that are mimicked as disclosed herein. As the ordinary skilled person understands, these conditions can vary based on the plant species as well as where the plant is located (that is, the environment in which the plant is growing—e.g., macroenvironment). The environment around the plant will have an impact on the choice of conditions to be mimicked. Thus, a plant can be growing, for example, under a high humidity to low humidity conditions, high heat to low heat conditions, high light to low light conditions, or conditions of drought to flood conditions, and the like. These factors not only affect the plant but their environment experienced by plant pathogens. A further consideration is the plant microenvironment, which constitutes the environment of a small group of plants down to the environment experienced by a single plant. The conditions that a fungal pathogen or a bacterial pathogen may experience on the surface of a plant can be a combination of the effects of microenvironment and the macroenvironment. For example, a bacterial pathogen or a fungal on the surface of plant and prior to entry into the plant will likely find conditions of low nutrient availability (e.g., low nitrogen and/or low carbohydrate levels) on the plant surface. The humidity may be low due to dry surrounding conditions. These and other factors are taken into account when developing media for mimicking infections conditions for microbes on plant surfaces.

In some embodiments, the plant can include, but is not limited to, an angiosperm, a gymnosperm, a bryophyte, a fern and/or fern ally. In some embodiments, the plant can be a cell, plant and/or plant part of any plant species. Non-limiting examples of plants useful with the methods of the present invention include turf grasses, vegetable crops, including artichokes, kohlrabi, arugula, leeks, asparagus, lettuce (e.g., head, leaf, romaine), malanga, melons (e.g., muskmelon, watermelon, crenshaw, honeydew, cantaloupe), cole crops (e.g., brussels sprouts, cabbage, cauliflower, broccoli, collards, kale, chinese cabbage, bok choy), cardoni, carrots, napa, okra, onions, celery, parsley, chick peas, parsnips, chicory, peppers, potatoes, cucurbits (e.g., marrow, cucumber, zucchini, squash, pumpkin), radishes, dry bulb onions, rutabaga, eggplant, salsify, escarole, shallots, endive, garlic, spinach, green onions, squash, greens, beet (sugar beet, fodder beet), sweet potatoes, swiss chard, horseradish, tomatoes, turnips, and spices; a fruit and/or vine crop such as apples, apricots, cherries, nectarines, peaches, pears, plums, prunes, cherry, quince, almonds, chestnuts, filberts, pecans, pistachios, walnuts, citrus, blueberries, boysenberries, cranberries, currants, loganberries, raspberries, strawberries, blackberries, grapes, avocados, bananas, kiwi, persimmons, pomegranate, pineapple, tropical fruits, pomes, melon, mango, papaya, and lychee, a field crop plant such as clover, alfalfa, evening primrose, meadow foam, corn/maize (field, sweet, popcorn), hops, jojoba, peanuts, rice, safflower, small grains (barley, oats, rye, wheat, etc.), sorghum, tobacco, kapok, a leguminous plant (beans, lentils, peas, soybeans), an oil plant (rape, mustard, poppy, olive, sunflower, coconut, castor oil plant, cocoa bean, groundnut), *Arabidopsis*, a fiber plant (cotton, flax, hemp, jute), lauraceae (cinnamon, camphor), or a plant such as coffee, sugar cane, tea, and natural rubber plants; and/or a bedding plant such as a flowering plant, a cactus, a succulent and/or an ornamental plant, as well as trees such as forest (broad-leaved trees and evergreens, such as conifers), fruit, ornamental, and nut-bearing trees, as well as shrubs and/or other nursery stock.

In some embodiments, a fungal cell or a bacterial cell can be from any fungal genera or bacterial genera that can cause disease and infection (i.e., is pathogenic) in a plant. Non-limiting examples of fungal plant pathogens include *Alternaria* spp., *Aspergillus* spp., *Botryodiplodia* spp., *Botrytis* spp., *Cercospora* spp., *Cladosporium* spp., *Claviceps* spp., *Cochliobolus* spp., *Colletotrichum* spp., *Diaporthe* spp., *Diplodia* spp., *Drechslera* spp., *Erysiphe* spp., *Fusarium* spp., *Gibberella* spp., *Glomerella* spp., *Helminthosporium* spp., *Leptosphaeria* spp., *Leucostoma* spp., *Magnaporthe* spp., *Mucor* spp., *Mycosphaerella* spp., *Nectria* spp., *Oidium* spp., *Phoma* spp., *Phyllosticta* spp., *Pleospora* spp., *Podosphaera* spp., *Puccinia* spp., *Ramularia* spp., *Rhizoctonia* spp., *Schizophyllum* spp., *Sclerotinia* spp., *Sclerotium* spp., *Septoria* spp., *Thielaviolsis* spp., *Tilletia* spp., *Uromyces* spp., *Ustilago* spp., or *Verticillium* spp. Examples of plant pathogenic fungal species useful with this invention include, but are not limited to, *Alternaria brassicola, Alternaria dianthi, Alternaria alternata, Alternaria raphani, Aspergillus niger, Botryodiplodia umicola, Botryodiplodia ocidii, Botrytis cinerea, Botrytis fabae, Botrytis narcissicola, Cercospora apii, Cercospora beticola, Cercospora kikuchii, Cladosporium arthropodii, Cladosporium cladosporoides, Claviceps purpurea, Cochliobolus carbonum, Cochliobolus sativus, Colletotrichum glycines, Colletotrichum orbiculare, Colletotrichum pisi, Colletotrichum trifoli, Diaporthe helianthi, Diaporthe perniciosa, Diaporthe phaeolorum, Diplodia seriata, Drechslera avenacea, Erysiphe graminis, Fusarium solani, Fusarium graminearum, Fusarium oxysporum, Fusarium pallidoroseum, Fusarium sacchari, Gibberella avenacea, Gibberella acuminata, Gibberella fujikuroi, Gibberella zeae, Glomerella cingulata, Helminthosporium cookei, Helminthosporium solani, Leptosphaeria acuta, Leptosphaeria maculans, Leptosphaeria sacchari, Leucostoma auerswaldii, Leucostoma kunzei, Magnaporthe grisea, Mucor circinelloides, Mucor hiemalis, Mucor piriformis, Mucor citricolor, Mycosphaerella terrestris, Mycosphaerella brassicicola, Mycosphaerella dendroides, Mycosphaerella graminicola, Mycosphaerella polymorpha, Mycosphaerella pyri, Nectria cinnabarina, Nectria radicicola, Oidium indicum, Oidium mangiferae, Phoma nebulosa, Phoma microspora, Phoma sclerotioides, Phyl-*

*losticta batatas, Phyllosticta carpogena, Phyllosticta nicotianae, Phyllosticta perseae, Pleospora herbarum, Pleospora lycopersici, Pleospora thea, Podosphaera leucotricha, Puccinia aristidae, Puccinia coronata, Puccinia erianthi, Puccinia hordei, Puccinia malvacearum, Puccinia purpurea, Puccinia xanthii, Ramularia menthicola, Rhizoctonia leguminicola, Rhizoctonia solani, Rhizoctonia solani, Schizophyllum commune, Sclerotinia borealis, Sclerotinia minor, Sclerotinia spermophila, Sclerotium cinnomomi, Sclerotium spermophila, Septoria bataticola, Septoria glycines, Septoria helianthi, Septoria pisi, Thielaviolsis basicola, Tilletia tritici, Uromyces beticola, Uromyces graminis, Uromyces pisi-sativi, Uromyces musae, Ustilago hordei, Ustilago esculenta, Ustilago maydis, Ustilago tritici, Verticillium albo-atrum, Verticillium dahliae, Verticillium alfalfae, Verticillium longisporum,* or *Verticillium theobromae.*

Non-limiting examples of bacterial plant pathogens include *Acetobacter* spp., *Agrobacterium* spp., *Arthrobacter* spp., *Bacillus* spp., *Clavibacter* spp., *Clostridium* spp., *Corynebacterium* spp., *Erwinia* spp., *Nocardia* spp., *Pseudomonas* spp., *Serratia* spp., *Streptomyces* spp., *Xanthomonas* spp., or *Xylella* spp. Examples of species of plant pathogenic bacteria useful with this invention include, but are not limited to, *Acetobacter aceti, Acetobacter pasteurianus, Agrobacterium radiobacter, Agrobacterium rhizogenes, Agrobacterium rubi, Agrobacterium tumefaciens, Arthrobacter ilicis, Bacillus megaterium, Bacillus pumilus, Clavibacter iranicus, Clavibacter rathayi, Clavibacter tritici, Clavibacter xyli, Clostridium puniceum, Corynebacterium beticola, Corynebacterium flaccumfaciens, Corynebacterium michiganensis, Erwinia chrysanthemi, Erwinia paradisiaca, Erwinia cancerogena, Erwinia dissolvens, Erwinia carotovora, Erwinia herbicola, Erwinia pyrofoliae, Erwinia rhapontici, Erwinia stewartii, Nocardia vaccinii, Pseudomonas agarici, Pseudomonas amygdali, Pseudomonas avenae, Pseudomonas corrugate, Pseudomonas gladioli, Pseudomonas marginalis, Pseudomonas savastanoi, Pseudomonas syringae, Pseudomonas savastanoi, Serratia proteamaculans, Streptomyces acidiscabies, Streptomyces candidus, Streptomyces intermedius, Streptomyces reticuliscabei, Xanthomonas arboricola, Xanthomonas alfalfae, Xanthomonas campestris, Xanthomonas citri,* or *Xylella fastidiosa.*

Additionally provided are media that mimic conditions at an infection site in an organism. For example, when the organism is an animal, optionally a mammal, the media that mimic conditions at an infection site can mimic conditions of cerebral spinal fluid, blood, epidermal surface, mucosal surface (eye, mouth, intestine, genital tract, nasal tract), lung surface, brain tissue, bladder, kidney, wound, or other organ or tissue, and the conditions can mimic cerebral spinal fluid, blood, epidermal surface, mucosal surface (eye, mouth, intestine, genital tract, nasal tract), lung surface, brain tissue, bladder, kidney, a wound, and/or other organ or tissue. In particular embodiments, the invention provides media that mimics cerebral spinal fluid comprising low nitrogen and low carbohydrate (e.g., low glucose). In further embodiments, when the organism is a plant, the media that mimic conditions at an infection site can mimic conditions on a plant surface (leaf, stem, flower, root, fruit), in phloem, in xylem, or within and/or between a plant's cells (i.e., intracellular and/or intercellular), and/or in or on other plant tissue types. In still further embodiments, the media that mimic conditions at an infection site can mimic conditions in the soil.

The invention further provides a method of treating a fungal infection in an organism, comprising administering to an organism in need thereof a therapeutically effective amount of validamycin A. In some embodiments, the organism can be an animal and the fungal infection can be caused by *Cryptococcus* spp., *Candida* spp., *Mucor* spp., and/or *Apergillus* spp, optionally the fungal infection can be caused by *Cryptococcus neoformans, Candida albicans, Candida tropicalis, Mucor circinelloides,* and/or *Aspergillus fumigatus.* In some embodiments, the organism can be a plant and the fungal infection is not caused by *Rhizoctonia* spp., optionally not by *Rhizoctonia solani.* In representative embodiments, the plant is not rice and the fungal infection is not caused by *Rhizoctonia* spp., optionally not by *Rhizoctonia solani.*

An additional aspect of the invention provides a method of identifying one or more antiproliferative molecular targets in a mammalian cancer cell, comprising: growing the mammalian cancer cell in vitro under cancer mimetic conditions; identifying genes that are upregulated in the mammalian cancer cell when grown under cancer mimetic conditions as compared to the mammalian cancer cell grown in vitro under standard or clinical laboratory conditions.

A further aspect of the invention provides a method of identifying a compound having antiproliferative activity, comprising: growing a mammalian cancer cell in vitro under cancer mimetic conditions in the presence or absence of a test compound; and selecting a compound that reduces the growth of (e.g., reduce the rate of cell division) or kills the mammalian cancer cell as compared to the mammalian cancer cell grown in vitro under cancer mimetic conditions in the absence of the compound.

A still further aspect of the invention provides a method of identifying a compound having antiproliferative activity against a mammalian cancer cell in a clinical sample, comprising culturing the clinical sample or a portion of the clinical sample in vitro under conditions that mimic a site of cancer proliferation in the presence or absence of a test compound; and selecting a compound that reduces the growth of (e.g., reduce the rate of cell division) or kills the mammalian cancer cell in the clinical sample as compared to the mammalian cancer cell grown in vitro under cancer mimetic conditions in the absence of the compound.

A clinical sample can be prepared by removing a portion of tissue from a patient/subject and culturing the portion of tissue on a plate or in a dish in a cancer mimetic medium, wherein the growth conditions provided by the cancer mimetic media (e.g., temperature, pH, nutrients, etc) mimic those in the organism, for example at the site of cancer proliferation in the organism.

An exemplary mammalian cancer cell includes a carcinoma cell, sarcoma cell, lymphoma cell, leukemia cell, or germinoma cell. In other embodiments, the mammalian cancer cell includes, but is not limited to, a pancreatic cancer cell, liver cancer cell, colon cancer cell, breast cancer cell, cervical cancer cell, vaginal cancer cell, testicular cancer cell, skin cancer cell, prostate cancer cell, mouth cancer cell, bone cancer cell, esophageal cancer cell, lymphoma cell, leukemia cell, lung cancer cell, colon cancer cell, rectal cancer cell, kidney cancer cell, brain cancer cell, and gastric cancer cell.

In some embodiments, the growth conditions for the mammalian cancer cell mimic conditions at a site of cancer proliferation (i.e., cancer mimetic conditions). In some embodiments, the site of cancer proliferation can be, but is not limited to, blood, pancreas, liver, colon, breast, cervix, vagina, testicle, skin, prostate, lymph node, lung, rectum, esophagus, mouth, bone, colon, kidney, brain, stomach, a wound and/or other organ or tissue. In representative embodiments, the clinical sample can be obtained from the site of cancer proliferation or it can be obtained from another site in/on the organism. In some embodiments, the growth conditions for the mammalian cancer cell mimic conditions at, for example, the site of solid tumors and/or leukemias/lymphomas in blood, pancreas, liver, colon, breast, cervix, vagina, testicle, skin, prostate, lymph node, lung, rectum, esophagus, mouth, bone, colon, kidney, brain, stomach, a wound, and/or other organ or tissue.

In some embodiments, the site of cancer proliferation can be the stomach, wherein the cancer cell is a stomach cancer cell, and the cancer mimetic conditions comprise a media comprising high pH, *Heliobacter pylori* infection, low oxygen, and restricted nutrients.

The invention further provides a cancer mimetic media that mimics conditions at a site of cancer growth in a mammal.

In some embodiments, a cancer mimetic condition for a solid tumor can include, for example, low sodium, low oxygen (e.g., hypoxic), low carbohydrate, and low available nitrogen. A cancer mimetic condition for a blood cancer, lymphoma or leukemia can include, for example, normal sodium levels, increased temperature (e.g., fever), low carbohydrate, elevated pH, and low nitrogen. See, Table 1 for exemplary infection mimetic conditions for media of this invention.

TABLE 2

Exemplary cancer mimetic conditions

| Mimetic Condition | Solid Tumor | Blood Cancer Lymphoma or Leukemia |
|---|---|---|
| Salt Content | Low NaCl (<135 mM) [16] | 150 mM NaCl |
| Temperature | 37° C. | >37° C. [17] |
| Oxygen levels | Hypoxic | Normoxic |
| pH | ~7.0 [19] | ~7.35 |
| Carbohydrate Content | Lactate 6-10 µM/g [22] Glucose 5.5 mM | Glucose 5.5 mM |
| Nitrogen Content | Free Amino Acids [24] | Free Amino Acids [24] |
| Extracellular Matrix | Matrix Metaloproteases Collagen Fibronectin | None |
| Other cell types in co-culture | Cancer Stem Cells Normal Mesenchymal Cells | No |
| Hormones or Cytokines | Tumor Dependent | No |

The invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

EXAMPLES

Example 1

Several studies demonstrate how fungal cells (*S. cerevisiae*) respond differently to optimized growth conditions vs. nutrient depleted conditions. Gene expression programs are markedly different when cells are dividing slowly in media depleted for a variety of nutrients. Interestingly, the GRR (Growth Rate Regulated) response (the profile of up-regulated and down-regulated genes) is very similar, regardless of which nutrient is depleted. Moreover, the set of GRR genes was found to substantially overlap with a set of genes (Environmental Stress Response; ESR) that are up- or down-regulated in response to a variety of stresses (e.g. osmotic stress). Genes that exhibited positive correlation with growth rate tended to be genes inhibited by stress, while genes that were down-regulated in fast growth conditions were often activated by stress. As well, there was considerable overlap between the GRR gene set and the YMC responsive gene sets. Thus, these yeast cells appear to mount a similar gene expression response to either low nutrients (GRR) or a variety of stresses (Stress Response Genes) that is disjoint from the gene expression program observed in cells dividing rapidly in optimized growth conditions.

Studies that employed a chemostat in which the growth/division rate of cells can be precisely controlled revealed that the gene expression patterns of the GRR are dynamic, and oscillate in a program referred to as the Yeast Metabolic Cycle (YMC). It has been recognized or some time that metabolic processes in yeast are periodically regulated and may be coordinated with the cell cycle. When budding yeast cells are grown in continuous culture conditions (chemostat) at appropriate densities and growth rates, the cells synchronize in robust metabolic cycles that can be monitored by periodic changes in dissolved oxygen.

By sampling continuous cultures of metabolically synchronous populations of budding yeast over time, investigators have identified oscillations in gene expression that are coincident with the periodicity of the yeast metabolic cycle (YMC). The reported periods of the YMC can vary substantially, and seem to be linked to growth rate. The YMC regulates a large transcriptional program and appears to be coordinated with the cell cycle under slow growth conditions. In a recent study using continuous culture conditions and a variety of nutritional limitations, researchers demonstrated that all of the GRR transcripts were, in fact, periodic during the YMC. Taken together, these findings suggest that the mechanisms controlling oscillation in transcript abundance are integrating signals from stress, growth rate, YMC and cell cycle.

The salient question is whether this dynamic program of gene expression in response to nutrient limitation and stress is simply a response to nutrient limitation or stress, or whether its execution is essential for continued growth and division under these slow growth conditions.

In studies aimed at understanding how metabolic mutations that alter growth rates regulate the cell division clock, rho$^0$ mutants were used that lack mitochrondrial DNA, and thus, are forced to ferment sugar sources rather than do oxidative phosphorylation. These mutant cells are metabolically perturbed and grow slowly (primarily in G1). By performing time series transcriptomic experiments in a cell-cycle synchronized time series experiment in batch culture, we found that these cells were going through both cell cycle oscillations and metabolic oscillations (YMC). This is an exciting finding, as the integration of the two cycles has been difficult to interrogate in chemostat culture systems.

Two distinct and coupled cycling programs of gene expression were identified in cells growing in rho$^0$ mutant cells that were growing slowly. Using algorithms to identify periodic behaviors, we identified two distinct sets of oscillatory programs. These two programs are depicted in FIG. 1.

Figure 2:
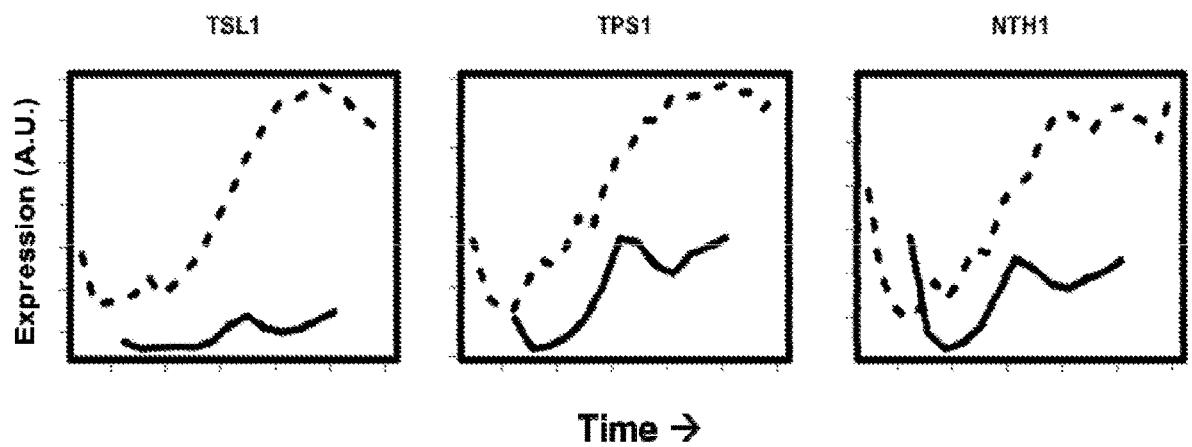
FIG. 2 shows genes in the trehalose metabolism pathway are up-regulated and oscillate strongly only in the stress conditions in *S. cerevisiae*. mRNA levels (arbitrary expression units) for 3 trehalose pathway genes (TSL1, TPS1, and NTH1) are shown over time in a cell-cycle synchronized population of cells harboring mutations that impair oxidative metabolism (dotted) and in wild-type cells (solid).

The cell cycle oscillation depicted on the lower left is common to cells growing in optimized or nutrient non-limiting conditions. The metabolic oscillations on the lower right are found only in metabolic mutants or in cells in limiting nutrient conditions. Within the metabolic oscillation program, we discovered that genes for an entire metabolic pathway (trehalose storage and utilization) were expressed periodically at very high levels in the rho$^0$ mutants, but were not observed to be elevated in normal cells (FIG. 2). A variety of sources suggest a model in which cells growing under metabolically stressful conditions store and burn trehalose in order to continue cycling [6,11]. Thus, the trehalose pathway may be one important connection between the cell cycle clock and the YMC, and may be a pathway that is essential for cell division in metabolic mutants or in nutrient-limited media.

Figure 3:
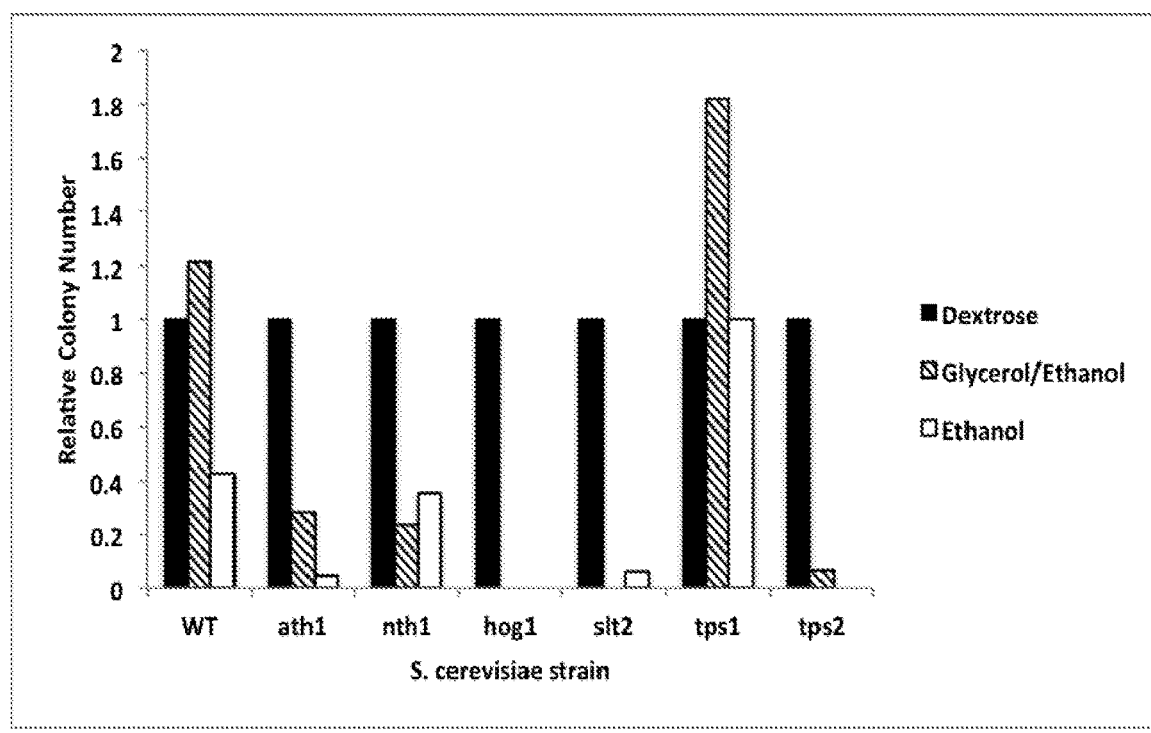
FIG. 3 shows that cell division is severely inhibited in slow growth medium in deletion mutants. Equal numbers of wild-type (WT) cells and cells deleted for various genes were grown in rich media (YEP+2% (w/v) Dextrose) over night, inoculated and diluted into rich defined medium (Yeast Nitrogen Base supplemented with essential amino acids+2% (w/v) Dextrose) or in nutrient limiting defined media (Yeast Nitrogen Base supplemented with essential amino acids+3% (v/v) Glycerol/3% (v/v) Ethanol or 3% (v/v) Ethanol only) at equal concentrations and grown for 24 hours. Equal volumes of medium containing WT or mutant cells were then plated on YEP+2% (w/v) Dextrose plates to determine the number of viable cells. After 48 hours, colonies were counted and results shown are relative to the number of colonies observed after growth in rich medium.

To test whether genes of the trehalose pathway might be essential for growth in nutrient-limiting conditions, we made knockout mutants in several genes of the trehalose pathway including TPS1, TPS2 (trehalose synthases) as well as NTH1 (trehalase). We then monitored growth in nutrient limiting media (Glycerol or Glycerol/Ethanol). As shown in FIG. 3, deletion of the trehalose pathway genes did not impair growth in optimal growth medium (YEP+2% (w/v) dextrose) but three out of four of the mutations (tps2, ath1, nth1) severely inhibited growth in nutrient-limiting medium (SC-Ethanol). Furthermore, we could not knock out these genes in rho$^0$ cells, suggesting they are required for growth of metabolically disabled mutants.

These genetic knockout experiments support the hypothesis that at least some genes expressed differentially in nutrient-depleted conditions (as compared to optimized growth conditions) may be required for growth in the nutrient-depleted conditions. If these nutrient-depleted, slow growth conditions mimic the slow growth, stressful conditions encountered by pathogens in an in vivo infection, then it is likely that there is an array of potential drug targets that would have been missed during screens in optimized growth conditions. Strikingly, tps1 tps2 Δ knockout mutants in the fungal pathogen, *Cryptococcus neoformans*, have been shown to be essentially avirulent in a rabbit meningitis model system [12]. Since the current thinking in the field is that the role of trehalose in virulence is related to the osmotic stabilization of proteins, rather than being an essential fuel source when cells are growing in nutrient-depleted conditions, the potential relevance of this fact has been missed.

Example 2

Novel Pharmacological Screens Using Infection-Mimetic Growth Conditions

While optimizing screening protocols for speed and low cost has obvious benefits both in research and clinical settings, screening conditions that are optimized for speed and cost often bear little resemblance (if any) to the conditions encountered by cells during the infection of a human host. For example, during an infection, *C. neoformans* yeast cells grow and divide in the cerebral spinal fluid (CSF) of infected patients. CSF is low in glucose and nitrogen, and during infection, the host temperature is elevated, leading to slow division of the yeast cells [13]. By contrast, the standardized primary in vitro screening conditions (i.e., standard laboratory conditions) are much higher in glucose and nitrogen, and cells are grown at lower temperatures to stimulate rapid growth. Thus, the growth conditions encountered by the yeast cells during infection are very different than those encountered in standardized screening protocols.

The inventors have discovered that the transcriptional activation or repression of some fraction of the genes controlling the cell cycle is important for cell division in the face of limiting nutrients or stress, that is, the activation or repression of this fraction of genes is important when the organism enters in the slow growth mode. Furthermore, most of the conditions likely to be encountered by microbes attempting to divide in a host during an infection scenario are sub-optimal and force cells to divide slowly. The same appears to be true for tumor cells growing in a solid tumor lacking an adequate blood supply. Genes in pathways important for division in sub-optimal growth conditions represent viable drug targets for anti-microbial or anti-proliferative compounds targeted at the organisms whose slow growth programs involve expression of these genes.

Figure 4:
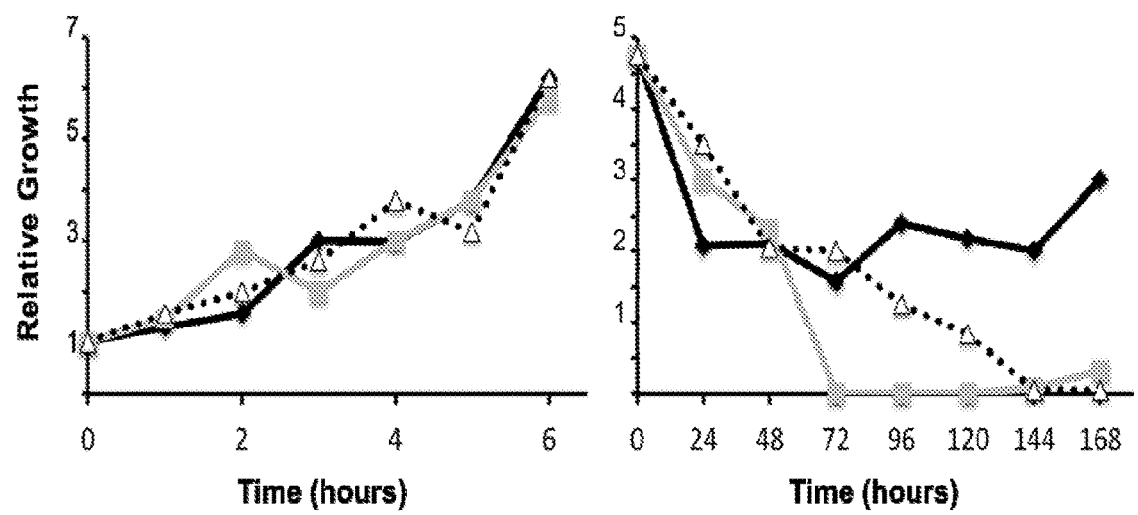
FIG. 4 shows growth of *Cryptococcus neoformans* is inhibited in slow growth medium but not rich medium. Left panel: *C. neoformans* cells were grown in rich medium (YEP+2% (w/v) Dextrose) with 0 mM (black), 50 mM (gray), and 100 mM (dotted) concentrations of Validamycin A. Cells were counted each hour for 6 hours and relative growth per mL was assessed. Right panel: *C. neoformans* cells were grown for 24 hours in PUD media and then dosed with Validamycin A. Cells were grown in slow growth medium (PUD) with 0 mM (black), 50 mM (gray), and 100 mM (dotted) concentrations of Validamycin A for 7 days and then counted at time intervals shown. Media was changed every 24 hours to fresh media containing the indicated concentration of drug.

Here, we determined whether a trehalose-mimetic compound (Validamycin A) produced by a *Streptomyces* bacterium, could target the trehalose pathway in *S. cerevisiae* and in *C. neoformans*, and inhibit their cell division in sub-optimal growth conditions. Validamycin A had no effect on division rates in optimal growth conditions (YEPD+2% (w/v) Dextrose), but severely inhibited division rates in slow growth conditions (PUD medium; PBS, 5 g/L Urea, supplemented with 0.1% (w/v) dextrose was used, which mimics nutrient conditions in cerebral spinal fluid) (FIG. 4). Plating assays indicate that Validamycin A is fungicidal in these conditions, as colony forming units are substantially reduced when cells are exposed to Validamycin A under slow growth conditions.

Mutants in the trehalose pathway do not exhibit the rapid division phenotype in optimal growth conditions, suggesting that SFG1 functions in a distinct genetic pathway that normally restrains division in sub-optimal growth conditions. Based on our collection of gene expression data and genetic knockout experiments, we predict that there are multiple genes and pathways that are essential for slow division in sub-optimal growth conditions. We expect these pathways to be involved in, for example: (1) the metabolism of storage carbohydrates that accumulate in nutrient depleted growth media. (e.g., genes involved in trehalose storage, transport, and metabolism including: TPS2, NTH1, NTH2); (2) the prevention of cell-cycle entry until sufficient nutrients and energy have been stored. (e.g., genes such as SFG1); and (3) the protection of cellular components from stresses induced by metabolic pathways specific to slow growth (including oxidative and osmotic stresses) (e.g., genes such as HOG1 and SLT2, and Rad53).

When mutated, the gene encoding Sfg1 has a phenotype similar (but not identical) to the trehalose pathways. Mutant cells where the Sfg1 gene has been deleted (sfg1Δ) exhibit a more rapid division rate than wild-type cells in optimal growth conditions, but are severely impaired for division in sub-optimal growth conditions. These findings suggest that SFG1 may play a role in restraining entry into the cell division cycle in response to slow growth conditions.

We have every reason to believe our discoveries in *S. cerevisiae* and *C. neoformans* will be applicable to other important fungal pathogens, including but not limited to, *Candida albicans, Candida tropicalis, Mucor* species such as *Mucor circinelloides*, and *Aspergillus fumigatus*.

Previous studies have investigated the efficacy of Validamycin A in preventing the growth of *Candida albicans* [14] and concluded that Validamycin A is not effective as an antifungal agent against *C. albicans*. These experiments were performed in rich medium and fit with our discovery that screening conditions are likely important in determining in vitro and in vivo efficacy of anti-fungal agents.

Trehalose has been shown to be an important molecule for the growth and virulence of pathogenic bacteria in the genus *Mycobacteria*, including *Mycobacterium tuberculosis*. *Mycobacteria* in general are extremely slow growing and often refractory to antibiotic treatments. It is not clear whether trehalose pathways are part of a slow-division pathway in *Mycobacteria*, but these findings suggest that genetic pathways essential for slow division may exist in bacterial species in addition to fungi. Thus, the application of our infection mimetic growth conditions to bacterial species may yield new insights into novel antibiotic targets [28].

Example 3

Drug Sensitivity Testing in Slow Growth Conditions

Figure 5:
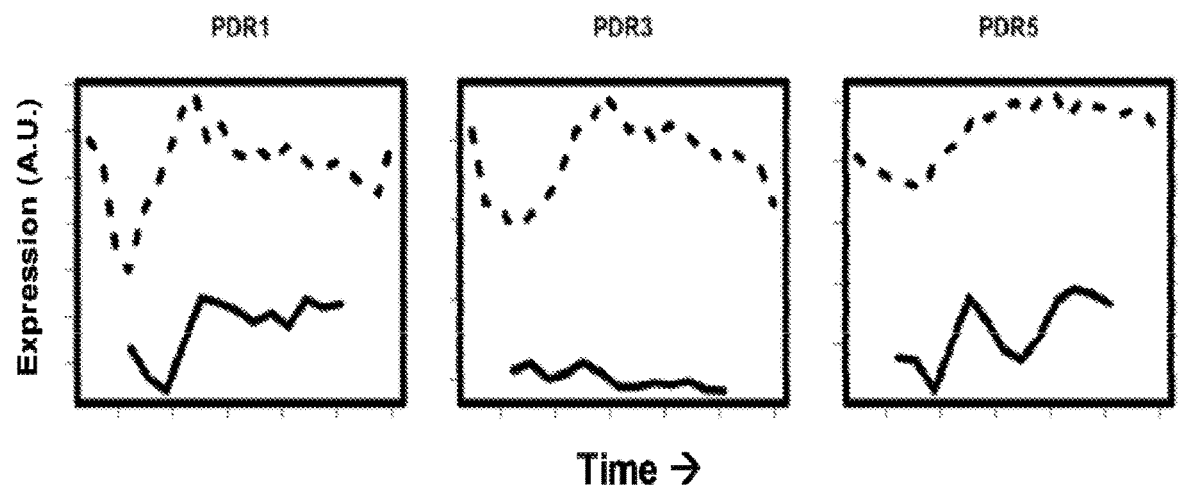
FIG. 5 shows Pleiotropic Drug Resistance (PDR) genes are up-regulated in metabolically crippled *S. cerevisiae* cells ($rho^0$). Synchronized $rho^0$ cells (as described in FIG. 1) exhibit up-regulated expression (dashed line) of a multi-drug resistance pump (PDR5) as well as genes encoding transcription factors that control pump gene expression (PDR1, PDR3). The expression is compared to synchronized wild type ($rho^+$) cells (solid line).

Screening clinical isolates for drug sensitivity is an important aspect of a clinical treatment protocol. Growth conditions for clinical screening are very specific [15] and utilize growth-optimized conditions that likely do not reflect in vivo conditions in the infected patient. Our experiments have revealed that several genes encoding multidrug resistance-like pumps are up-regulated when fungal cells are exposed to slow-growth conditions (see, FIG. 5). Here, Pleiotropic Drug Resistance (PDR) genes are up-regulated in metabolically crippled *S. cerevisiae* cells (rho$^0$). Synchronized rho$^0$ cells (as described in FIG. 1) exhibit up-regulated expression (dashed line) of a multi-drug resistance pump (PDR5) as well as genes encoding transcription factors that control pump gene expression (PDR1, PDR3). Thus, it is expected that the up-regulation of these pumps could contribute to drug resistance in vivo, but not in growth-optimized conditions (i.e., standard laboratory conditions). Thus, conditions used for clinical screening for drug sensitivity/resistance may be further optimized by an additional screening step performed in infection mimetic conditions as described herein.

The foregoing is illustrative of the present invention, and is not to be construed as limiting thereof. The invention is defined by the following claims, with equivalents of the claims to be included therein.

REFERENCES

1. Fothergill, A. W., Rinaldi, M. G., and Sutton, D. A. (2006). Antifungal susceptibility testing. Infectious disease clinics of North America 20, 699-709.
2. Brauer, M. J., Huttenhower, C., Airoldi, E. M., Rosenstein, R., Matese, J. C., Gresham, D., Boer, V. M., Troyanskaya, O. G., and Botstein, D. (2008) Coordination of growth rate, cell cycle, stress response, and metabolic activity in yeast. *Mol Biol Cell* 19, 352-367.
3. Gasch, A. P., Spellman, P. T., Kao, C. M., Carmel-Harel, O., Eisen, M. B., Storz, G., Botstein, D., and Brown, P. O. (2000). Genomic expression programs in the response of yeast cells to environmental changes. *Mol Biol Cell* 11, 4241-4257.
4. Slavov, N., and Botstein, D. (2011). Coupling among growth rate response, metabolic cycle, and cell division cycle in yeast. *Mol Biol Cell* 22, 1997-2009.
5. Tu, B. P., Kudlicki, A., Rowicka, M., and McKnight, S. L. (2005). Logic of the yeast metabolic cycle: temporal compartmentalization of cellular processes. *Science* 310, 1152-1158.
6. Futcher, B. (2006). Metabolic cycle, cell cycle, and the finishing kick to start. *Genome Biol* 7, 107.
7. Creanor, J. (1978). Carbon dioxide evolution during the cell cycle of the fission yeast *Schizosaccharomyces pombe*. *J Cell Sci* 33, 385-397.
8. Novak, B., and Mitchison, J. M. (1986). Change in the rate of CO2 production in synchronous cultures of the fission yeast *Schizosaccharomyces pombe*: a periodic cell cycle event that persists after the DNA-division cycle has been blocked. *J Cell Sci* 86, 191-206.
9. Novak, B., and Mitchison, J. M. (1990). Changes in the rate of oxygen consumption in synchronous cultures of the fission yeast *Schizosaccharomyces pombe*. *J Cell Sci* 96 (Pt 3), 429-433.
10. Klevecz, R. R., Bolen, J., Forrest, G., and Murray, D. B. (2004). A genomewide oscillation in transcription gates DNA replication and cell cycle. *Proc Natl Acad Sci USA* 101, 1200-1205.
11. Haase, S. B., and Wittenberg, C. (2014). Topology and control of the cell-cycle-regulated transcriptional circuitry. *Genetics* 196, 65-90.
12. Petzold, E. W., Himmelreich, U., Mylonakis, E., Rude, T., Toffaletti, D., Cox, G. M., Miller, J. L., and Perfect, J. R. (2006). Characterization and regulation of the trehalose synthesis pathway and its importance in the pathogenicity of *Cryptococcus neoformans*. *Infection and immunity* 74, 5877-5887.
13. Mandal, R., Guo, A. C., Chaudhary, K. K., Liu, P., Yallou, F. S., Dong, E., Aziat, F., and Wishart, D. S. (2012). Multi-platform characterization of the human cerebrospinal fluid metabolome: a comprehensive and quantitative update. *Genome medicine* 4, 38.
14. Guirao-Abad, J. P., Sanchez-Fresneda, R., Valentin, E., Martinez-Esparza, M., and Arguelles, J. C. (2013). Analysis of validamycin as a potential antifungal compound against *Candida albicans*. *Intl Microbiol* 16, 217-225.
15. Cuenca-Estrella, M., Gomez-Lopez, A., Alastruey-Izquierdo, A., Bernal-Martinez, L., Cuesta, I., Buitrago, M. J., and Rodriguez-Tudela, J. L. (2010). *J Clin. Microbiol.* 48, 1782-1786.
16. Onitilo A A, Kio E, Doi S A R: *Clinical Medicine & Research* 2007, 5:228-237.
17. Peng L H, Keng T C, Sinniah D: *Cancer* 1981, 47:583-587.
18. Luft F C, Rissing J P, White A, Brooks G F: *Am J Med Sci* 1976, 272:65-74.
19. Tannock I F, Rotin D: *Cancer Res* 1989, 49:4373-4384.
20. Merril C R, Seipp H W, Luchsinger P C: *J Appl Physiol* 1961, 16:485-487.
21. Gethin G: *Wounds uk* 2007, 3:52.
22. Walenta S, Wetterling M, Lehrke M, Schwickert G, Sundfør K, Rofstad E K, Mueller-Klieser W: *Cancer Research* 2000, 60:916-921.
23. Mandal R, Guo A C, Chaudhary K K, Liu P, Yallou F S, Dong E, Aziat F, Wishart D S: *Genome Medicine* 2012, 4:1-11.
24. Canepa A, Divino Filho J C, Gutierrez A, Carrea A, Forsberg A M, Nilsson E, Verrina E, Perfumo F, Bergström J: *Nephrology Dialysis Transplantation* 2002, 17:413-421.
25. Sunderkötter C, Steinbrink K, Goebeler M, Bhardwaj R, Sorg C: *Journal of Leukocyte Biology* 1994, 55:410-422.
26. Rubin-Bejerano I, Abeijon C, Magnelli P, Grisafi P, Fink G R: *Cell host & microbe* 2007, 2:55-67.
27. Madhani H D, Fink G R: *Trends Cell Biol* 1998, 8:348-353.

28. Nobre, A., Alarico, S., Maranha, A., Mendes, V., and Empadinhas, N. (2014). *Microbiology.* 160(Pt8), 1547-70.

That which is claimed is:

1. A method of identifying one or more antimicrobial molecular targets in a budding yeast cell comprising:

growing the budding yeast cell in vitro under infection mimetic conditions to produce a metabolically synchronous population of budding yeast cells;

sampling continuous cultures of the metabolically synchronous population of budding yeast cells over time; and identifying genes that are differentially regulated in the metabolically synchronous population of the budding yeast cells when grown in vitro under the infection mimetic conditions as compared to the budding yeast cells grown in vitro under standard laboratory conditions, wherein the infection mimetic conditions are of a site of an infection by the budding yeast cell, and the site of the infection is in an animal.

2. The method of claim 1, wherein the infection mimetic conditions mimic blood of the infected animal and comprise growing the budding yeast cell in a growth media comprising 150 mM NaCl, 5.5 mM glucose, free amino acids, macrophages, neutrophils, and human serum factors at a temperature of greater than 37° C. and a pH of <7.35 with normoxic oxygen levels.

3. The method of claim 1, wherein the infection mimetic conditions mimic a wound infection in the animal and comprise growing the budding yeast cell in a media comprising less than 150 mM NaCl, 5.5 mM glucose, free amino acids, collagen, elastin, fibronectin macrophages, neutrophils, interleukin, and tumor necrosis factor at a temperature of greater than 37° C. and a pH ranging from 7.15 to 8.9 with hypoxic oxygen levels.

4. The method of claim 1, wherein the infection mimetic conditions mimic cerebral spinal fluid of the infected animal and comprise growing the budding yeast cell in a media comprising phosphate buffered saline (PBS), 5 g/L of urea and 0.1% dextrose or in a media comprising 150 mM NaCl, 3 mM glucose, and 4 mM urea at a temperature of greater than 37° C. and a pH of about 7.35 with normoxic oxygen levels.

5. The method of claim 1, wherein the budding yeast cell is a *Cryptococcus* spp., *Candida* spp., or *Mucor* spp.

\* \* \* \* \*